US010345298B2

(12) United States Patent
Hemmer et al.

(10) Patent No.: US 10,345,298 B2
(45) Date of Patent: Jul. 9, 2019

(54) DIAGNOSIS OF MULTIPLE SCLEROSIS

(71) Applicant: Klinikum rechts der Isar der Technischen Universität München, München (DE)

(72) Inventors: Bernhard Hemmer, München (DE); Rajneesh Srivastava, München (DE); Lucas Schirmer, München (DE)

(73) Assignee: Klinikum rechts der Isar der Technischen Universität München, München (DE)

( * ) Notice: Subject to any disclaimer, the term of this patent is extended or adjusted under 35 U.S.C. 154(b) by 0 days.

(21) Appl. No.: 15/306,344

(22) PCT Filed: Apr. 30, 2015

(86) PCT No.: PCT/EP2015/059531
§ 371 (c)(1),
(2) Date: Oct. 24, 2016

(87) PCT Pub. No.: WO2015/166057
PCT Pub. Date: Nov. 5, 2015

(65) Prior Publication Data
US 2017/0074877 A1  Mar. 16, 2017

(30) Foreign Application Priority Data

Apr. 30, 2014 (EP) .................... 14166705

(51) Int. Cl.
*G01N 33/564* (2006.01)
(52) U.S. Cl.
CPC ..... *G01N 33/564* (2013.01); *G01N 2800/285* (2013.01)
(58) Field of Classification Search
None
See application file for complete search history.

(56) References Cited

U.S. PATENT DOCUMENTS 9,134,323 B2 * 9/2015 MacKinnon ......... G01N 33/566
9,297,809 B2 * 3/2016 Hemmer ................ C07K 16/28

FOREIGN PATENT DOCUMENTS

| EP | 239 400 | 8/1994 |
| EP | 2530088 | 12/2012 |
| WO | WO 89/09622 | 10/1989 |
| WO | WO 91/10741 | 7/1991 |
| WO | WO 94/02602 | 2/1994 |
| WO | WO 96/33735 | 10/1996 |
| WO | WO 96/34096 | 10/1996 |
| WO | WO 02/18650 | 3/2002 |
| WO | WO 2012/163765 | 12/2012 |

OTHER PUBLICATIONS

N. Eng. J. Med 2012 vol. 367, p. 115-123 The Supplementary Appendix total 30 pages (Year: 2012).*
Ascherio et al., "Environmental Risk Factors for Multiple Sclerosis. Part I: The Role of Infection", *Ann. Neurol.*, vol. 61, No. 4, pp. 288-299, 2007.
Ascherio et al., "Environmental Risk Factors for Multiple Sclerosis. Part II: Noninfectious Factors", *Ann. Neurol.*, vol. 61, No. 6, pp. 504-513, 2007.
Galfre et al., "Preparation of Monoclonal Antibodies: Strategies and Procedures", *Methods in Enzymology*, vol. 73, 45 pages, 1981.
Hafler et al., "Risk Alleles for Multiple Sclerosis Identified by a Genomewide Study," *The New England Journal of Medicine*, vol. 357, No. 9, pp. 851-862, 2007.
Jung et al., "Lines of Murine Oligodendroglial Precursor Cells Immortalized by an Activated neu Tyrosine Kinase Show Distinct Degrees of Interaction with Axons In Vitro and In Vivo," *European Journal of Neuroscience*, vol. 7, pp. 1245-1265, 1995.
Kohler et al., "Continuous Cultures of Fused Cells Secreting Antibody of Predefined Specificity", *Nature*, vol. 256, pp. 495-497, 1975.
Malmborg et al., "BIAcore as a Tool in Antibody Engineering," *Journal of Immunological Methods*, vol. 183, pp. 7-13, 1995.
McFarland et al., "Multiple Schlerosis: A Complicated Picture of Autoimmunity", *Nature Immunology*, vol. 8, pp. 913-919, 2007.
Noseworthy et al., "Multiple Schlerosis", *The New England Journal of Medicine*, vol. 343, pp. 938-952, 2000.
PCT International Search Report and Written Opinion for PCT/EP2015/059531 dated Jun. 22, 2015 (12 pages).
Schier et al., "Efficient in vitro Affinity Maturation of Phage Antibodies Using BIAcore Guided Selections", *Human Antibodies Hybridomas*, vol. 7, pp. 97-105, 1996.
Srivastava et al., "Potassium Channel KIR4.1 as an Immune Target in Multiple Sclerosis", *New England Journal of Medicine*, vol. 367, No. 2, pp. 115-123, Jul. 12, 2012.
Thrower et al., "Clinically Isolated Syndromes", *Neurology*, vol. 68, pp. S12-S15, 2007.

* cited by examiner

*Primary Examiner* — Changhwa J Cheu
(74) *Attorney, Agent, or Firm* — Mueting, Raasch & Gebhardt, P.A.

(57) ABSTRACT

The present invention relates to a method for diagnosing multiple sclerosis (MS) and/or clinically isolated syndrome (CIS) and/or radiologically isolated syndrome (RIS) or a predisposition for either condition in a subject, the method comprising determining the presence of an anti-KIR4.1 antibody in a sample obtained from said subject by (a) contacting said sample with a protein; and (b) detecting the formation of a protein-anti-KIR4.1 antibody complex; wherein said protein is KIR4.1, wherein glycosylation of the large extracellular domain of said KIR4.1 is as in human oligodendrocytes or glycosylation of the large extracellular domain is absent; and wherein the formation of said complex is indicative of MS, CIS, RIS or a predisposition therefore. Furthermore provided is an antibody or fragment or derivative thereof competing with the anti-KIR4.1 antibody in a sample obtained from a patient having MS.

5 Claims, 5 Drawing Sheets
Specification includes a Sequence Listing.

Figure 3:
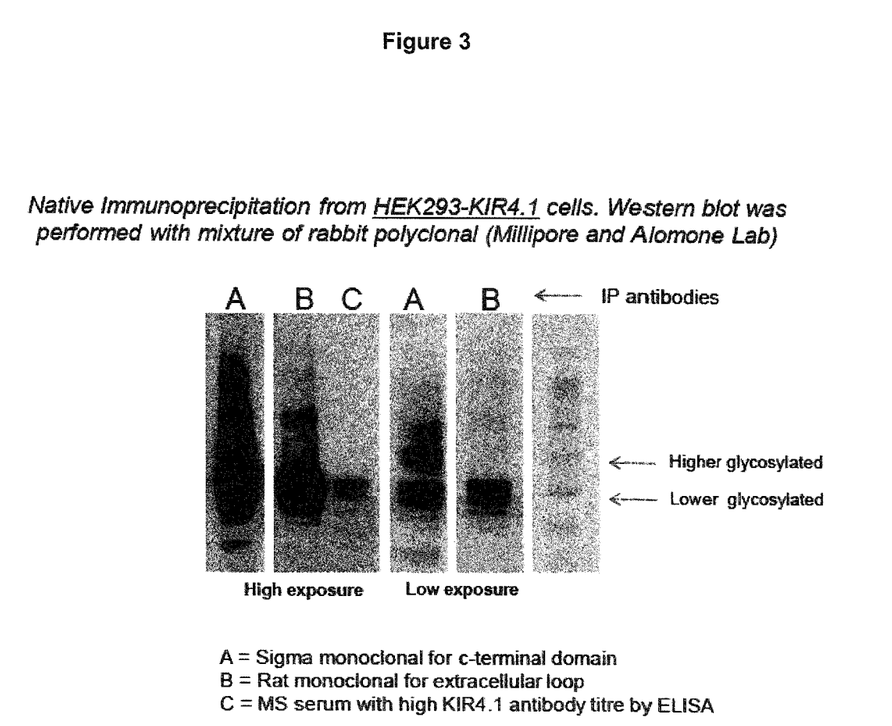
FIG. 3: Sigma mouse mAb (A) targeting the C-terminal domain capture a broad range of KIR4.1 proteins including highly glycosylated KIR4.1. By contrast, the rat mAb (B) targeting the extracellular domain of KIR4.1 and MS sera (C) pull predominantly the 38-42 kD isoform of KIR4.1.

*Native Immunoprecipitation from HEK293-KIR4.1 cells. Western blot was performed with mixture of rabbit polyclonal (Millipore and Alomone Lab)*

A = Sigma monoclonal for c-terminal domain
B = Rat monoclonal for extracellular loop
C = MS serum with high KIR4.1 antibody titre by ELISA

SEQUENCE LISTING

<160> NUMBER OF SEQ ID NOS: 17

<210> SEQ ID NO 1
<211> LENGTH: 5

```
<212> TYPE: PRT
<213> ORGANISM: Artificial Sequence
<220> FEATURE:
<223> OTHER INFORMATION: KIR4.1 fragment

<400> SEQUENCE: 1

Asp Pro Pro Ala Asn
1               5

<210> SEQ ID NO 2
<211> LENGTH: 15
<212> TYPE: PRT
<213> ORGANISM: Artificial Sequence
<220> FEATURE:
<223> OTHER INFORMATION: KIR4.1 fragment

<400> SEQUENCE: 2

Ala His Gly Asp Leu Leu Glu Leu Asp Pro Pro Ala Asn His Thr
1               5                  10                  15

<210> SEQ ID NO 3
<211> LENGTH: 379
<212> TYPE: PRT
<213> ORGANISM: Homo sapiens

<400> SEQUENCE: 3

Met Thr Ser Val Ala Lys Val Tyr Tyr Ser Gln Thr Thr Gln Thr Glu
1               5                   10                  15

Ser Arg Pro Leu Met Gly Pro Gly Ile Arg Arg Arg Val Leu Thr
                20                  25                  30

Lys Asp Gly Arg Ser Asn Val Arg Met Glu His Ile Ala Asp Lys Arg
                35                  40                  45

Phe Leu Tyr Leu Lys Asp Leu Trp Thr Thr Phe Ile Asp Met Gln Trp
    50                  55                  60

Arg Tyr Lys Leu Leu Leu Phe Ser Ala Thr Phe Ala Gly Thr Trp Phe
65                  70                  75                  80

Leu Phe Gly Val Val Trp Tyr Leu Val Ala Val Ala His Gly Asp Leu
                85                  90                  95

Leu Glu Leu Asp Pro Pro Ala Asn His Thr Pro Cys Val Val Gln Val
                100                 105                 110

His Thr Leu Thr Gly Ala Phe Leu Phe Ser Leu Glu Ser Gln Thr Thr
                115                 120                 125

Ile Gly Tyr Gly Phe Arg Tyr Ile Ser Glu Glu Cys Pro Leu Ala Ile
                130                 135                 140

Val Leu Leu Ile Ala Gln Leu Val Leu Thr Thr Ile Leu Glu Ile Phe
145                 150                 155                 160

Ile Thr Gly Thr Phe Leu Ala Lys Ile Ala Arg Pro Lys Lys Arg Ala
                165                 170                 175

Glu Thr Ile Arg Phe Ser Gln His Ala Val Val Ala Ser His Asn Gly
                180                 185                 190

Lys Pro Cys Leu Met Ile Arg Val Ala Asn Met Arg Lys Ser Leu Leu
                195                 200                 205

Ile Gly Cys Gln Val Thr Gly Lys Leu Leu Gln Thr His Gln Thr Lys
                210                 215                 220

Glu Gly Glu Asn Ile Arg Leu Asn Gln Val Asn Val Thr Phe Gln Val
225                 230                 235                 240

Asp Thr Ala Ser Asp Ser Pro Phe Leu Ile Leu Pro Leu Thr Phe Tyr
                245                 250                 255
```

```
His Val Val Asp Glu Thr Ser Pro Leu Lys Asp Leu Pro Leu Arg Ser
            260                 265                 270

Gly Glu Gly Asp Phe Glu Leu Val Leu Ile Leu Ser Gly Thr Val Glu
        275                 280                 285

Ser Thr Ser Ala Thr Cys Gln Val Arg Thr Ser Tyr Leu Pro Glu Glu
    290                 295                 300

Ile Leu Trp Gly Tyr Glu Phe Thr Pro Ala Ile Ser Leu Ser Ala Ser
305                 310                 315                 320

Gly Lys Tyr Ile Ala Asp Phe Ser Leu Phe Asp Gln Val Val Lys Val
            325                 330                 335

Ala Ser Pro Ser Gly Leu Arg Asp Ser Thr Val Arg Tyr Gly Asp Pro
        340                 345                 350

Glu Lys Leu Lys Leu Glu Glu Ser Leu Arg Glu Gln Ala Glu Lys Glu
    355                 360                 365

Gly Ser Ala Leu Ser Val Arg Ile Ser Asn Val
        370                 375

<210> SEQ ID NO 4
<211> LENGTH: 38
<212> TYPE: PRT
<213> ORGANISM: Homo sapiens

<400> SEQUENCE: 4

Gly Val Val Trp Tyr Leu Val Ala Val Ala His Gly Asp Leu Leu Glu
1               5                   10                  15

Leu Asp Pro Pro Ala Asn His Thr Pro Cys Val Val Gln Val His Thr
            20                  25                  30

Leu Thr Gly Ala Phe Leu
        35

<210> SEQ ID NO 5
<211> LENGTH: 44
<212> TYPE: DNA
<213> ORGANISM: Artificial Sequence
<220> FEATURE:
<221> NAME/KEY: source
<222> LOCATION: 1..44
<223> OTHER INFORMATION: /mol_type="unassigned DNA"
      /note="Primer"
      /organism="Artificial Sequence"

<400> SEQUENCE: 5
gcggccgcac catgacgtca gttgccaagg tgtattacag tcag            44

<210> SEQ ID NO 6
<211> LENGTH: 45
<212> TYPE: DNA
<213> ORGANISM: Artificial Sequence
<220> FEATURE:
<221> NAME/KEY: source
<222> LOCATION: 1..45
<223> OTHER INFORMATION: /mol_type="unassigned DNA"
      /note="Primer"
      /organism="Artificial Sequence"

<400> SEQUENCE: 6
ctcgagtcag tggtggtggt ggtggtggac attgctgatg cgcac           45

<210> SEQ ID NO 7
<211> LENGTH: 6
<212> TYPE: PRT
<213> ORGANISM: Artificial Sequence
<220> FEATURE:
```

-continued

<223> OTHER INFORMATION: KIR4.1 fragment

<400> SEQUENCE: 7

Leu Asp Pro Pro Ala Asn
1               5

<210> SEQ ID NO 8
<211> LENGTH: 7
<212> TYPE: PRT
<213> ORGANISM: Artificial Sequence
<220> FEATURE:
<223> OTHER INFORMATION: KIR4.1 fragment

<400> SEQUENCE: 8

Glu Leu Asp Pro Pro Ala Asn
1               5

<210> SEQ ID NO 9
<211> LENGTH: 8
<212> TYPE: PRT
<213> ORGANISM: Artificial Sequence
<220> FEATURE:
<223> OTHER INFORMATION: KIR4.1 fragment

<400> SEQUENCE: 9

Leu Glu Leu Asp Pro Pro Ala Asn
1               5

<210> SEQ ID NO 10
<211> LENGTH: 9
<212> TYPE: PRT
<213> ORGANISM: Artificial Sequence
<220> FEATURE:
<223> OTHER INFORMATION: KIR4.1 fragment

<400> SEQUENCE: 10

Leu Leu Glu Leu Asp Pro Pro Ala Asn
1               5

<210> SEQ ID NO 11
<211> LENGTH: 10
<212> TYPE: PRT
<213> ORGANISM: Artificial Sequence
<220> FEATURE:
<223> OTHER INFORMATION: KIR4.1 fragment

<400> SEQUENCE: 11

Asp Leu Leu Glu Leu Asp Pro Pro Ala Asn
1               5                   10

<210> SEQ ID NO 12
<211> LENGTH: 11
<212> TYPE: PRT
<213> ORGANISM: Artificial Sequence
<220> FEATURE:
<223> OTHER INFORMATION: KIR4.1 fragment

<400> SEQUENCE: 12

Gly Asp Leu Leu Glu Leu Asp Pro Pro Ala Asn
1               5                   10

<210> SEQ ID NO 13
<211> LENGTH: 12
<212> TYPE: PRT
<213> ORGANISM: Artificial Sequence
<220> FEATURE:
<223> OTHER INFORMATION: KIR4.1 fragment

```
<400> SEQUENCE: 13

His Gly Asp Leu Leu Glu Leu Asp Pro Pro Ala Asn
1               5                   10

<210> SEQ ID NO 14
<211> LENGTH: 13
<212> TYPE: PRT
<213> ORGANISM: Artificial Sequence
<220> FEATURE:
<223> OTHER INFORMATION: KIR4.1 fragment

<400> SEQUENCE: 14

Ala His Gly Asp Leu Leu Glu Leu Asp Pro Pro Ala Asn
1               5                   10

<210> SEQ ID NO 15
<211> LENGTH: 20
<212> TYPE: PRT
<213> ORGANISM: Artificial Sequence
<220> FEATURE:
<223> OTHER INFORMATION: KIR4.1 fragment

<400> SEQUENCE: 15

Lys Leu Glu Glu Ser Leu Arg Glu Gln Ala Glu Lys Glu Gly Ser Ala
1               5                   10                  15

Leu Ser Val Arg
            20

<210> SEQ ID NO 16
<211> LENGTH: 6
<212> TYPE: PRT
<213> ORGANISM: Artificial Sequence
<220> FEATURE:
<223> OTHER INFORMATION: KIR4.1 fragment

<400> SEQUENCE: 16

Pro Pro Ala Asn His Thr
1               5

<210> SEQ ID NO 17
<211> LENGTH: 4
<212> TYPE: PRT
<213> ORGANISM: Artificial Sequence
<220> FEATURE:
<223> OTHER INFORMATION: KIR4.1 fragment

<400> SEQUENCE: 17

Pro Pro Ala Asn
1
```

DIAGNOSIS OF MULTIPLE SCLEROSIS

This application is a U.S. National Stage Application of International Application No. PCT/EP2015/059531, filed Apr. 30, 2015, which was published in English on Nov. 5, 2015, as International Publication No. WO 2015/166057 A1. International Application No. PCT/EP2015/059531 claims priority to European Application No. 14166705.5, filed Apr. 30, 2014.

The present invention relates to a method for diagnosing multiple sclerosis (MS), clinically isolated syndrome (CIS) and/or radiologically isolated syndrome (RIS) or a predisposition for either condition in a subject, the method comprising determining the presence of an anti-KIR4.1 antibody in a sample obtained from said subject by (a) contacting said sample with a protein or peptide; and (b) detecting the formation of a protein-anti-KIR4.1 antibody complex or a peptide-anti-KIR4.1 antibody complex, respectively; wherein said protein is KIR4.1, wherein glycosylation of the large extracellular domain of said KIR4.1 is as in human oligodendrocytes or glycosylation of the large extracellular domain is absent; wherein said peptide (i) consists of a subsequence of the large extracellular domain of human KIR4.1, (ii) which subsequence is at least 5 consecutive amino acid residues long, (iii) which subsequence comprises or consists of SEQ ID NO: 1 or 2, and (iv) wherein the residue N of SEQ ID NO: 1 or 2 is glycosylated as the corresponding N residue of the large extracellular domain of KIR4.1 of human oligodendrocytes or is not glycosylated; and wherein the formation of said complex is indicative of MS, CIS, RIS or a predisposition therefore.

In this specification, a number of documents including patent applications and manufacturer's manuals is cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Multiple sclerosis (MS) is the most common chronic inflammatory disease of the central nervous system (CNS) leading to disability in the majority of affected patients (Noseworthy et al., N. Engl. J. Med. 343, 938-952 (2000)). The etiology of MS is unknown but epidemiological evidence suggests a complex interplay between genetic and environmental factors (Ascherio et al., Ann. Neurol. 61, 504-513 (2007); Ascherio et al., Ann. Neurol. 61, 288-299 (2007); Hafler et al., N. Engl. J. Med. 357, 851-862 (2007)). An uncertain pathogenic mechanism, clinical heterogeneity and unpredictability of the outcome of individual patients add to the complexity of the disease (McFarland et al., Nat. Immunol. 8, 913-919 (2007)).

In WO 2012/163765, the present inventors disclosed that KIR4.1, a specific inward rectifying potassium channel is involved in the etiology of multiple sclerosis. More specifically, a subset of multiple sclerosis patients has anti-KIR4.1 autoantibodies in its serum.

In the present application, the present inventors investigated further into possibilities for sensitively detecting said autoantibodies. In doing so, the inventors aimed to provide improved means and methods for the diagnosis of multiple sclerosis. In particular, it turned out that the presence vs. absence and in particular nature of glycosylation of KIR4.1 influences antibody binding.

In a first aspect, the present invention relates to a method for diagnosing multiple sclerosis (MS), clinically isolated syndrome (CIS) and/or radiologically isolated syndrome (RIS) or a predisposition for either condition in a subject, the method comprising determining the presence of an anti-KIR4.1 antibody in a sample obtained from said subject by (a) contacting said sample with a protein or peptide; and (b) detecting the formation of a protein-anti-KIR4.1 antibody complex or a peptide-anti-KIR4.1 antibody complex, respectively; wherein said protein is KIR4.1, wherein glycosylation of the large extracellular domain of said KIR4.1 is as in human oligodendrocytes or glycosylation of the large extracellular domain is absent; wherein said peptide (i) consists of a subsequence of the large extracellular domain of human KIR4.1, (ii) which subsequence is at least 5 consecutive amino acid residues long, (iii) which subsequence comprises or consists of SEQ ID NO: 1 or 2, and (iv) wherein the residue N of SEQ ID NO: 1 or 2 is glycosylated as the corresponding N residue of the large extracellular domain of KIR4.1 of human oligodendrocytes or is not glycosylated; and wherein the formation of said complex is indicative of MS, CIS, RIS or a predisposition therefore.

In a preferred embodiment glycosylation of the large extracellular domain of said KIR4.1 is as in human oligodendrocytes.

The term "peptide" refers to a polycondensate of amino acids. Preferably, said amino acids are selected from the 20 naturally occurring amino acids. The upper length limit of the peptide of the present invention is given by the limitation that the peptide is a subsequence of the large extracellular domain of KIR4.1, wherein, in a preferred embodiment, the length of said extracellular domain is defined by the length of SEQ ID NO: 4.

Said subsequence which is at least 5 consecutive amino acid residues long is preferably at least 6, at least 7, at least 8, at least 9, at least 10, at least 11, at least 12, at least 13, at least 14 or at least 15 consecutive amino acid residues long. A preferred subsequence which is exactly 15 consecutive amino acid residues long is the sequence of SEQ ID NO: 2. In further preferred embodiments, said subsequence has a length of at least 20, at least 25, at least 30 or at least 35 consecutive amino acid residues. Said subsequence may also consist of or comprise any one of SEQ ID NOs: 7 to 14. Subsequences comprising any one of SEQ ID NOs: 7 to 14 include subsequences consisting of a sequence of any one of SEQ ID NOs: 7 to 14 wherein either His or His-Thr is added to the C-terminus.

A further preferred subsequence is that from residue 10 to residue 15 of SEQ ID NO: 2, herewith enclosed as SEQ ID NO: 16 (PPANHT).

In any of the above-defined peptides, 1 or more, preferably, 2, 3, 4, 5, 6, 7, 8, 9 or 10 amino acids may be replaced by other amino acids, provided that the sequence of SEQ ID NO: 1, which is comprised in any of the above-defined peptides, remains unaltered. To the extent any of the above-defined peptides comprises the sequence of SEQ ID NO: 2 in its entirety, it is preferred that the sequence of SEQ ID NO: 2 in its entirety remains unaltered.

The term "protein" has its art-established meaning. In particular, a protein can comprise one or more polypeptides. A polypeptide is a polycondensate of amino acids, wherein no particular length limit applies. A preferred protein in accordance with the present invention is a homotetramer. Proteins, even if they are monomeric, may differ from mere polycondensates of amino acids in that one or more posttranslational modifications are present. A key feature of the present invention is the posttranslational modification which is glycosylation. While the specific requirements of the present invention in terms of glycosylation are defined herein above and below, it is noted that further posttranslational modifications may be present or absent. Having regard to the protein of the present invention which is KIR4.1, it is preferred that in the large extracellular domain thereof there is exactly one site which is a target of post-translational modification. Said posttranslational modification is N-glycosylation, and it concerns a specific Asn residue as defined above.

It is noted that both protein and peptide according to the present invention are characterized in that they are capable of binding to the anti-KIR4.1 antibody which is present in the serum of a subgroup of multiple sclerosis patients. This antibody is also referred to as "autoantibody" herein. This autoantibody preferably recognizes an epitope comprising or consisting of SEQ ID NO: 17 (PPAN) which is comprised within SEQ ID NO: 2.

Said autoantibody is to be distinguished from a further antibody which is an antibody according to one of the aspects of the present invention detailed further below. The latter antibody is capable of competing with said autoantibody for binding to the same epitope in the large extracellular domain of KIR4.1.

Provided with the teaching of the present invention and that of the present inventors' earlier application WO 2012/163765, said autoantibody can be pulled down from the serum of patients having MS and purified. Suitable means for precipitating the antibody include the receptor and peptide as defined in WO 2012/163765 as well as the proteins and peptides according to the present invention.

The term "multiple sclerosis" refers to an inflammatory disease affecting the nervous system; see also the literature quoted in the background section above. Whether or not a subject or patient has multiple sclerosis can be determined with the method of diagnosing according to the invention. Alternatively or in addition, a diagnosis of multiple sclerosis can be established on the basis of established clinical symptoms, said clinical symptoms being known to the skilled person. The clinical symptoms of multiple sclerosis include vision problems, dizziness, vertigo, sensory dysfunction, weakness, problems with coordination, loss of balance, fatigue, pain, neurocognitive deficits, mental health deficits, bladder dysfunction, bowel dysfunction, sexual dysfunction, heat sensitivity. Diagnosis on the basis of said clinical symptoms, however, will generally be less sensitive as compared to the methods of the present invention. Moreover, in many cases predisposition will be characterized by the absence of any clinical symptoms in which case diagnosis of predisposition can only be effected by using the method of the present invention or, in the alternative, that of the present inventors' earlier invention described in WO 2012/163765.

CIS is generally perceived in the art as being an early stage MS, wherein the clinical parameters characteristic of the latter are not yet fully developed. For a discussion of CIS, see, for example, Thrower, Neurology 68, S12-S15 (2007).

Analogously, also radiologically isolated syndrome (RIS) is considered an early stage MS. RIS patients are patients who received an MRI of the brain for non-MS related reasons. The patient has MS-like lesions although the patient has not yet classical MS symptoms. These patients are diagnosed with RIS. They have an about 30% chance to develop MS within the next years.

The present inventors detected in earlier studies that high titers of anti-KIR4.1 autoantibodies are found in the serum of 50.8% of patients. Accordingly, the presence of anti-KIR4.1 autoantibodies defines a subgroup of MS patients. It is expected that this subgroup responds or responds particularly well to treatment with peptides according to the present invention. Determining whether a given individual belongs to this subgroup can be determined with the diagnostic means and methods as disclosed herein as well as in WO 2012/163765.

The method of the first aspect permits to diagnose multiple sclerosis, or, to the extent multiple sclerosis is not apparent in said subject, for diagnosing a predisposition therefore. The term "predisposition" has the meaning as established in the art and prefers a likelihood to develop a disease. In particular, said likelihood is higher than in a normal control subject. Said likelihood in a normal control subject may be represented as the average likelihood to develop MS in a random sample from the population.

A preferred group of individuals to be tested for said predisposition are individuals with a history of MS in the family.

Given that the present inventors detected high titers of anti-KIR4.1 antibodies in sera of a significant fraction of MS patients, the means and methods described herein allow diagnosis of MS or a predisposition therefore in about half of the MS cases or subjects being at risk to develop the disease, respectively. In particular, the methods of the invention permit early diagnosis of MS or a predisposition therefore or a confirmation of an uncertain diagnosis. The antibody test may allow to diagnose CIS or MS without invasive procedures (such as cerebrospinal fluid analysis) and to diagnose MS, CIS or predisposition to MS earlier than this would be possible by diagnostic procedures known in the art. It is well known that MS therapy works best when started as early as possible during the course of disease. Therefore, early diagnosis may allow to implement early treatment of patients with CIS, MS or at risk to develop these diseases. In some individuals at risk treatment may even prevent the (further) development of disease.

Said contacting is to be effected under conditions allowing the formation of the complex defined in item (b) of the first aspect. Exemplary or preferred conditions are described in the Examples enclosed herewith; see the section "KIR4.1 ELISA", as well as further below.

Detecting the formation of said complex can be done with art-established methods. Basically, methods for detecting the formation of a complex comprising an antigen and an antibody are applicable for that purpose. Preferred methods are detailed further below.

The present inventors discovered that, in the sequence of the large surface domain of KIR4.1, the epitope recognized by the anti-KIR4.1 autoantibody as present in the sera of MS patients includes a site for N-glycosylation. Furthermore, it turned out that presence vs. absence and in particular nature of glycosylation of the mentioned site influences antibody binding. In particular, high degrees of glycosylation caused less sensitive detection or may abrogate antibody binding altogether. A "high degree of glycosylation" refers to a large oligosaccharide moiety being bound. An exemplary highly glycosylated form has an apparent molecular weight of about 49 to about 55 kD on a denaturing gel. Therefore, for the assay for anti-KIR4.1 autoantibodies to be sensitive, the probe, i.e. the protein or peptide of the present invention, may be non-glycosylated. The non-glycosylated form of KIR4.1 from humans has an apparent molecular weight of about 34 kD on a denaturing gel. If non-glycosylated forms are to be obtained from glycosylated forms, this is preferably done by treatment with the enzyme peptide-N-glycosidase (PNGase).

Preferably, KIR4.1 and the protein of the invention is glycosylated only to a low degree, more specifically it is glycosylated as in human oligodendrocytes. The term "glycosylated as in human oligodendrocytes" refers to the presence of an oligosaccharide moiety which is identical or substantially identical to the oligosaccharide moiety which is present on human KIR4.1 as it occurs in human oligodendrocytes. The glycosylation site of human KIR4.1 is defined by SEQ ID NO: 1 or 2, more specifically by the N-residue thereof, noting that SEQ ID NO: 1 or 2 is a subsequence of the large extracellular domain of human KIR4.1. The N residue is comprised in a NXT motif for N glycosylation, residue X being H in case of KIR4.1. The sequence NHT forms the last three residues of SEQ ID NO: 16. On a denaturing gel, KIR4.1, when glycosylated as in human oligodendrocytes, has an apparent molecular weight of about 38 to about 42 kD, more preferably from about 40 to about 42 kD. Especially preferred is an apparent molecular weight of about 42 kD. The term "apparent molecular weight" refers, as usual, to the molecular weight on a denaturing gel.

While short peptides, when manufactured synthetically, will not be glycosylated, this does not apply for KIR4.1 as well as fragments thereof which are obtained from natural sources including cell lines. To the extent peptides and proteins from natural sources are to be used, it is therefore of utmost importance to pay attention to the degree of glycosylation.

To the extent glycosylation of said protein and said peptide is as in human oligodendrocytes, it is preferred that at least 80%, at least 85%, at least 90%, at least 91%, at least 92%, at least 93%, at least 94%, at least 95%, at least 96%, at least 97%, at least 98% and at least 99% of said protein or peptide is glycosylated as in human oligodendrocytes. More specifically, the large extracellular domain of said protein is glycosylated as in human oligodendrocytes, and the above-defined residue N is glycosylated as in human oligodendrocytes. Analogously, and to the extent use is to be made of non-glycosylated forms of said protein or said peptide, it is preferred that at least 80%, at least 85%, at least 90%, at least 91%, at least 92%, at least 93%, at least 94%, at least 95%, at least 96%, at least 97%, at least 98% and at least 99% is non-glycosylated, more specifically non-glycosylated in the large extracellular domain in case said protein is to be used, and non-glycosylated at the above-defined N residue in case use is to be made of said peptide. Having said that, it is also envisaged to use mixtures consisting of or comprising glycosylated and non-glycosylated forms, glycosylated forms being glycosylated as in human oligodendrocytes. To the extent such mixture is to be used, it is understood that preferably at least 80%, at least 85%, at least 90%, at least 91%, at least 92%, at least 93%, at least 94%, at least 95%, at least 96%, at least 97%, at least 98% and at least 99% of said mixture exclusively consist of the mentioned glycosylated and non-glycosylated forms.

Under physiological conditions, KIR4.1 occurs as a homotetramer. To the extent the assay in accordance with the first aspect of the present invention makes use of said protein, said protein preferably is in tetrameric form. Preferably, said peptide is in tetrameric form. Preference is given to those tetrameric forms of said peptide which mimic the tetrameric arrangement of epitopes as provided by the naturally occurring KIR4.1 homotetramer. Preferred epitopes are those defined by peptides comprising or consisting of SEQ ID NOs: 1 or 2. Envisaged is also the use of the monomeric form as well as of other oligomeric forms such as dimers, trimers, pentamers, hexamers etc, noting that the use of higher order aggregates is less preferred.

In a preferred embodiment, said anti-KIR4.1 antibody is present in said sample, (a) presence of at least one clinical symptom of MS, CIS or RIS in said subject is indicative of MS, CIS or RIS, respectively; and (b) absence of any clinical symptom of MS, CIS and RIS is indicative of said predisposition for MS, CIS and RIS.

As disclosed above, the methods according to the invention provide for diagnosing multiple sclerosis as well as for diagnosing a predisposition therefor. The present preferred embodiment provides for further information to be acquired for said subject, said further information aiding in distinguishing between diagnosis of the disease and diagnosis of a predisposition therefor. In particular, said further information consists of or comprises at least one clinical symptom of multiple sclerosis. Multiple sclerosis is a well-known disease with established clinical symptoms. The skilled person is well aware of clinical symptoms being characteristic or indicative of multiple sclerosis (see also above and below) and can determine the presence or absence thereof without further ado.

In accordance with the present preferred embodiment, the absence of any clinical symptom of multiple sclerosis, when concomitantly occurring together with the presence of anti-KIR4.1 antibodies, is indicative of predisposition for multiple sclerosis. In other words, where established methods of diagnosis or prognosis fail, the present invention allows to identify those subjects which exhibit an elevated risk of developing multiple sclerosis at some point in the future.

On the other hand, in subjects where at least one clinical symptom of multiple sclerosis is present, the determination of anti-KIR4.1 antibodies further corroborates the diagnosis of multiple sclerosis. In those cases where the clinical parameters alone do not permit a clear diagnosis, the present invention aids in performing and substantiating said diagnosis. This applies in particular to early forms of multiple sclerosis. As is well-known in the art, an early diagnosis of multiple sclerosis is highly desirable, given that early stages are generally more amenable to treatment.

According to a further preferred embodiment, said clinical symptom is at least one selected from vision problems, dizziness, vertigo, sensory dysfunction, weakness, problems with coordination, loss of balance, fatigue, pain, neurocognitive deficits, mental health deficits, bladder dysfunction, bowel dysfunction, sexual dysfunction, heat sensitivity, the presence of (an) inflammation marker(s) in cerebrospinal fluid (CSF), the presence of lesions of the brain and/or the spinal cord. The mentioned lesions may be detected in an MRT image. Typically, such lesions occur in the periventricular, juxtacortical and/or infratentorial region of the brain. Inflammation markers indicative of MS are well-known in the art and are preferably to be selected from pleocytosis (abnormally increased number of cells in the CSF, wherein typical values of increased cell numbers are between 5 and 50 cells/μl or above), intrathecal IgG synthesis and the occurrence of oligoclonal IgG bands in the CSF.

In a further preferred embodiment, the detection of the anti-KIR4.1 antibody or said complex, respectively, in said sample is effected by a method selected from the group consisting of ELISA, immunoprecipitation, Western blotting, immunofluorescence, immunohistochemistry, flow cytometry, metalloimmunoassay (such as GLORIA), fluorescence resonance energy transfer (FRET) assay and mass spectroscopy. These methods are well-established and at the skilled person's disposal. ELISA is particularly preferred. In an ELISA assay, an antibody binding to said anti-KIR4.1 antibody may be used. Similar considerations apply to immunoprecipitation, immunofluorescence and immunohistochemistry. As noted above, the skilled person, when provided with the teaching of the present invention, can isolate and characterize the anti-KIR4.1 antibody without further ado. Such characterization preferably uses mass spectrometry. Once being characterized, mass spectrometry may be used for determining presence or absence of anti-KIR4.1 antibodies in any given sample. FRET assays may be used, for example, in the context of a binding assay, said binding assay preferably making use of a receptor, said receptor being defined further below. Such FRET assay may be designed such that a detectable transfer between donor and acceptor of the FRET pair only occurs in case receptor and anti-KIR4.1 antibody are in close special proximity, said close special proximity being indicative of the presence of the anti-KIR4.1 antibody.

In a further preferred embodiment, said sample is selected from blood, serum, plasma, lymph nodes, CSF, lacrimal fluid, urine, sputum and brain biopsy.

In a further preferred embodiment, said protein or peptide is comprised in an in vitro cell, preferably in the cell membrane of said cell. In other words, it is preferred that the diagnostic assay in accordance with the first aspect of the present invention is implemented as a cell-based assay. It is especially preferred that said cells have the protein or peptide in accordance with the present invention incorporated into their cell membrane. This provides for the epitope present in said protein or peptide to be recognized and bound by the autoantibodies which are present in the sera of MS patients. It is preferred that said cell is also used to express the protein or peptide in accordance with the present invention.

In a second aspect, the present invention provides a protein wherein said protein is KIR4.1, and wherein glycosylation of the large extracellular domain of said KIR4.1 is as in human oligodendrocytes or absent.

The method according to the first aspect as disclosed herein above provides for the use of a protein or peptide, respectively, wherein both protein and peptide may be either non-glycosylated, in particular non-glycosylated at the Asn residue comprised in SEQ ID NO: 1 or 2, or may be glycosylated, in particular at said Asn in a manner which is identical or substantially identical to the glycosylation observed on human KIR4.1 in human oligodendrocytes. Preferred is the protein, and particularly preferred is the protein having a glycosylation status as in human oligodendrocytes. This is the subject-matter of the second aspect. We note that the glycosylation status in human oligodendrocytes, in particular at said Asn residue, is unique. The experimental data comprised in the examples provide further characterization of the glycosylation status of KIR4.1 as it is found in human oligodendrocytes, in particular in terms of the apparent molecular weight on a denaturing gel.

In a preferred embodiment of the method according to the first aspect as well as of the protein according to the second aspect, one or more of the following applies: (a) KIR4.1 is human KIR4.1; (b) said protein is a homotetramer of KIR4.1; (c) KIR4.1 consists of the amino acid sequence of SEQ ID NO: 3; (d) said extracellular domain consists of the amino acid sequence of SEQ ID NO: 4; and (e) glycosylation of the entire protein is as in human oligodendrocytes.

Human KIR4.1 occurs in its natural environment, including human oligodendrocytes, in a homotetrameric form. The sequence of human KIR4.1 is given in SEQ ID NO: 3. The sequence of the large extracellular domain thereof is given in SEQ ID NO: 4.

In a third aspect, the present invention provides a peptide (i) consisting of a subsequence of the large extracellular domain of human KIR4.1, (ii) which subsequence is at least 5 consecutive amino acid residues long, (iii) which subsequence comprises or consists of SEQ ID NO: 1 or 2, and (iv) wherein the residue N of SEQ ID NO: 1 or 2 is glycosylated as the corresponding N residue of the large extracellular domain of KIR4.1 of human oligodendrocytes.

As noted above, said peptide is an alternative to said protein. In particular, it is envisaged that said peptide mimics said protein. The Examples enclosed herewith provide a proof of principle that the salient features of said protein which are key for the method of diagnosis of the invention are indeed reproduced by said peptide.

In any of the above-defined peptides, 1 or more, preferably, 2, 3, 4, 5, 6, 7, 8, 9 or 10 amino acids may be replaced by other amino acids, provided that the sequence of SEQ ID NO: 1, which is comprised in any of the above-defined peptides, remains unaltered. To the extent any of the above-defined peptides comprises the sequence of SEQ ID NO: 2 in its entirety, it is preferred that the sequence of SEQ ID NO: 2 in its entirety remains unaltered.

We note that the present inventors' earlier application WO 2012/163765 also describes peptides, including peptides related to the large extracellular domain of human KIR4.1. The specific contribution of the present invention, however, is the recognition of the specific requirements of the assay in terms of glycosylation of the peptide for the assay to perform optimal. This is reflected by the third aspect of the present invention.

In a preferred embodiment of all above disclosed aspects of the present invention, said protein or peptide is obtained from human oligodendrocytes or from a cell line of oligodendrocytic origin such as Oli-neu oligodendrocytes.

Oligodendrocytes, also known as oligodendroglia, are cells of the central nervous system of certain vertebrates including humans. Their functions include the provision of support and insulation to axons.

As an alternative to oligodendrocytes, cells or cell lines of oligodendrocytic origin may be used as source of the protein or peptide according to the present invention. A particularly preferred cell line, said cell line being of oligodendrocytic origin, are Oli-neu cells (Jung et al. European Journal of Neuroscience, Vol. 7, pp. 1245-1265, 1995). Oli-neu cells as well as other cells of oligodendrocytic origin are known or expected, respectively, to provide the same type of N-linked glycosylation to KIR4.1 as well as peptides derived therefrom, i.e., proteins and peptides in accordance with the present invention. In a preferred embodiment, proteins or peptides in accordance with the present invention which are expressed from cells or cell lines of oligodendrocytic origin are (i) isolated as a single peak, preferably by means of gel filtration, which single peak corresponds to the tetrameric form, and/or (ii) analyzed on a denaturing gel in order to confirm that they have an apparent molecular weight of about 38 to about 42 kDa. Lower molecular weights may be acceptable as well.

In a fourth aspect, the present invention provides an antibody or fragment or derivative thereof competing with the anti-KIR4.1 antibody in a sample obtained from a patient having MS.

The present inventors used the peptide of SEQ ID NO: 2 for the purpose of raising an antibody. The most antigenic sequence within SEQ ID NO: 2 is the sequence of SEQ ID NO: 1. This is a first feature characterizing said antibody. A second feature characterizing said antibody is its capability to compete with the autoantibody. Furthermore, and similar to MS patients' autoantibodies, said antibody preferably binds with a binding affinity to KIR4.1 from human oligodendrocytes which binding affinity is higher than the binding affinity for lower or higher glycosylated forms. Said antibody is a useful constituent of the kit according to the present invention, which kit is disclosed further below.

As already noted above, it is preferred that said antibody binds to a peptide consisting of SEQ ID NO:1 or 2, wherein said peptide is either not glycosylated or glycosylated as the corresponding N residue of the large extracellular domain of KIR4.1 of human oligodendrocytes.

Antibodies as disclosed herein may be monoclonal or polyclonal antibodies. Furthermore, the term "antibody" includes single chain antibodies or fragments thereof that specifically bind to their respective target as well as bispecific antibodies, synthetic antibodies, antibody fragments such as Fab, F(ab$_2$)', Fv and scFv fragments and the like as well as chemically modified derivatives thereof.

Monoclonal antibodies can be prepared, for example, by the techniques as originally described in Köhler and Milstein, Nature 256 (1975), 495, and Galfré, Meth. Enzymol. 73 (1981), 3, which comprise the fusion of mouse myeloma cells to spleen cells derived from immunized mammals with modifications developed by the art. Furthermore, antibodies or fragments thereof to the aforementioned peptides can be obtained by using methods which are described, e.g., in Harlow and Lane "Antibodies, A Laboratory Manual", CSH Press, Cold Spring Harbor, 1988. When derivatives of said antibodies are obtained by the phage display technique, surface plasmon resonance as employed in the BIAcore system can be used to increase the efficiency of phage antibodies which bind to an epitope of the peptide or polypeptide of the invention (Schier, Human Antibodies Hybridomas 7 (1996), 97-105; Malmborg, J. Immunol. Methods 183 (1995), 7-13). The production of chimeric antibodies is described, for example, in WO89/09622. A further source of antibodies to be utilized in accordance with the present invention are so-called xenogenic antibodies. The general principle for the production of xenogenic antibodies such as human antibodies in mice is described in, e.g., WO 91/10741, WO 94/02602, WO 96/34096 and WO 96/33735. Antibodies to be employed in accordance with the invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook, Molecular Cloning: A Laboratory Manual, Cold Spring Harbor Laboratory, Cold Spring Harbor, N.Y., 1989.

The term "monoclonal" or "polyclonal antibody" (see Harlow and Lane, (1988), loc. cit.) also relates to derivatives of said antibodies which retain or essentially retain their binding specificity. Whereas particularly preferred embodiments of said derivatives are specified further herein below, other preferred derivatives of such antibodies are chimeric antibodies comprising, for example, a mouse or rat variable region and a human constant region.

The term "scFv fragment" (single-chain Fv fragment) is well understood in the art and preferred due to its small size and the possibility to recombinantly produce such fragments.

In a particularly preferred embodiment of the method of the invention, said antibody or antibody binding portion is or is derived from a human antibody or a humanized antibody. The term "humanized antibody" means, in accordance with the present invention, an antibody of non-human origin, where at least one complementarity determining region (CDR) in the variable regions such as the CDR3 and preferably all 6 CDRs have been replaced by CDRs of an antibody of human origin having a desired specificity. Optionally, the non-human constant region(s) of the antibody has/have been replaced by (a) constant region(s) of a human antibody. Methods for the production of humanized antibodies are described in, e.g., EP-A1 0 239 400 and WO90/07861.

In a fifth aspect, the present invention provides a kit comprising the above defined protein and/or the above defined peptide.

In a preferred embodiment, said kit further comprises one or more of (a) a manual containing instructions for performing the method of the first aspect; (b) an antibody in accordance with the fourth aspect of the present invention.

The present invention, in a sixth aspect, provides the use of the protein of the second aspect or of the peptide of the third aspect for removing anti-KIR4.1 antibodies from blood or serum of an MS, CIS or RIS patient or of a subject carrying a predisposition to develop MS, CIS or RIS, or reducing the amount of said antibodies, wherein said use is to be effected ex vivo.

Related thereto, the present invention provides an ex vivo method of removing anti-KIR4.1 antibodies from a bodily fluid such as blood or serum of an MS, CIS or RIS patient or of a subject carrying a predisposition to develop MS, CIS or RIS, or reducing the amount of said antibodies, wherein said use is to be effected ex vivo, said method comprising bringing blood removed from a subject into contact with a protein or peptide as defined above.

These aspects relate to ex vivo applications, said ex vivo applications aiming at a reduction of a number of autoantibodies or a complete depletion thereof. Preferably, blood or serum of an MS patient or of a subject carrying a predisposition to develop MS are subjected to the ex vivo treatment. It is understood that said bringing into contact is effected under conditions which allow binding of autoantibodies, if present, to said protein or peptide. In one embodiment, said conditions may be established by bringing into contact blood or serum with a carrier or device according to the invention, said carrier or device being further defined below.

In a preferred embodiment of the ex vivo method according to the invention, the blood or serum, after said bringing into contact, is to be returned to the same subject.

In further preferred embodiments of the ex vivo use or the ex vivo method of the invention, said protein or peptide is bound to a carrier. Any carrier, including a solid carrier is envisaged. Support or carrier materials commonly used in the art and comprising glass, plastic, gold and silicon are envisaged for the purpose of the present invention. Suitable coatings of the carrier or support, if present, include poly-L-lysine- and amino-silane-coatings as well as epoxy- and aldehyde-activated surfaces. In a preferred embodiment, said carrier is the matrix of a column. Suitable matrices are known in the art and may be derivatized by the attachment of said peptide.

The present invention furthermore relates to a carrier with a protein or peptide as defined above being immobilized thereon.

Related thereto, provided is also a device for removing anti-KIR4.1 antibodies from blood, said device comprising the carrier as defined above.

In a preferred embodiment of the device, said device further comprises an inlet and/or an outlet permitting to let blood or serum of the subject flow across the filter and/or the blood or serum being returned to the same subject.

As regards the embodiments characterized in this specification, in particular in the claims, it is intended that each embodiment mentioned in a dependent claim is combined with each embodiment of each claim (independent or dependent) said dependent claim depends from. For example, in case of an independent claim 1 reciting 3 alternatives A, B and C, a dependent claim 2 reciting 3 alternatives D, E and F and a claim 3 depending from claims 1 and 2 and reciting 3 alternatives G, H and I, it is to be understood that the specification unambiguously discloses embodiments corresponding to combinations A, D, G; A, D, H; A, D, I; A, E, G; A, E, H; A, E, I; A, F, G; A, F, H; A, F, I; B, D, G; B, D, H; B, D, I; B, E, G; B, E, H; B, E, I; B, F, G; B, F, H; B, F, I; C, D, G; C, D, H; C, D, I; C, E, G; C, E, H; C, E, I; C, F, G; C, F, H; C, F, I, unless specifically mentioned otherwise.

Similarly, and also in those cases where independent and/or dependent claims do not recite alternatives, it is understood that if dependent claims refer back to a plurality of preceding claims, any combination of subject-matter covered thereby is considered to be explicitly disclosed. For example, in case of an independent claim 1, a dependent claim 2 referring back to claim 1, and a dependent claim 3 referring back to both claims 2 and 1, it follows that the combination of the subject-matter of claims 3 and 1 is clearly and unambiguously disclosed as is the combination of the subject-matter of claims 3, 2 and 1. In case a further dependent claim 4 is present which refers to any one of claims 1 to 3, it follows that the combination of the subject-matter of claims 4 and 1, of claims 4, 2 and 1, of claims 4, 3 and 1, as well as of claims 4, 3, 2 and 1 is clearly and unambiguously disclosed.

The Figures show:

FIG. 4: (A-C) Costaining of the rat monoclonal antibody clone 20F9 with a commercial rabbit polyclonal anti-KIR4.1 antibody (Alomone, APC-035). Notably, clone 20F9 binds to aextracellular domain of KIR4.1 (peptide sequence AHGDLLELDPPANHT (SEQ ID NO: 2)), whereas the polyclonal commercial antibody binds to a intracellular C-terminal domain of KIR4.1 (peptide sequence KLEESLREQAEKEGSALSVR (SEQ ID NO: 15)). Clone 20F9 binds to a similar epitope that is bound by isolated anti-KIR4.1 IgG from serum obtained from MS patients. Note that 20F9 immunohistochemistry (IHC) on subcortical white matter control tissue displays predominantly a perinuclear and cell membrane staining pattern. Most of the staining seems to be restricted to cell bodies of oligodendrocytes (grey arrowheads) as confirmed by costaining with the commercial anti-KIR4.1 antibody. Of note, some astrocytes (white arrows) show a perinuclear staining with 20F9, however, it does not stain the majority of astrocytic cell bodies and fibers as observed with the commercial anti-KIR4.1 antibody. (D-F) Costaining of 20F9 with a commercial rabbit polyclonal anti-Olig2 antibody (IBL) confirms that 20F9 IHC predominantly has a perinuclear and cell membranes staining pattern in oligodendrocytes (arrowheads). Olig2 is an oligodendrocyte transcription factor. The anti-Olig2 antibody binds specifically to nuclei of oligodendrocytes and oligodendrocyte precursor cells. (G-I) Costaining of 20F9 with a mouse monoclonal anti-NogoA antibody (clone 11C7, gift from M. Schwab, Zurich) confirms that clone 20F9 binds to cytoplasms and cell membranes of mature oligodendrocytes (arrowheads). The anti-NogoA antibody binds specifically to cell bodies of mature oligodendrocytes. (J-L) Costaining of 20F9 with a commercial mouse monoclonal anti-GFAP antibody (Dako, 6F2) confirms that 20F9 staining is restricted to oligodendrocytes (GFAP negative, arrowheads) and perinuclear areas of a subset of astrocytes (white arrows, GFAP positive). Note that astrocyte in the center is not stained with 20F9.

The examples illustrate the invention.

EXAMPLE 1

Materials and Methods

For visualization of protein molecular weight in during electrophoresis and Western Blotting, Blue® Plus2 Pre-Stained Standard has been used.

Preparation of White Matter and Gray Matter Lysate

White matter or gray matter tissue were dissected from frozen human brain and weighed for equal amount (2.4 g). Tissue was homogenized using a glass tissue homogenizer in ice cold homogenization buffer (0.32M sucrose, 10 mM HEPES pH 7.4, 2 mM EDTA) and protease inhibitor cocktail (Sigma-Aldrich). The suspension was centrifuged at 1000 g to pellet down the nuclear fraction. High speed centrifugation and sucrose gradient method was used for the enrichment of the membrane fraction. The enriched membrane pellet was resuspended in HEPES solubilisation buffer (50 mM HEPES, 150 mMNaCl, 1.0% n-Dodecyl β-D-maltoside and protease inhibitor cocktail). The solubilised membrane protein extract were investigated further either with direct immunoblotting or immunoblotting of immunoprecipitated protein fractions. In case of KIR4.1 transient transfected (reverse method) HEK293 cells or wild type cell's total lysate were prepared with lysis buffer (50 mM HEPES, 150 mMNaCl, 1.0% n-Dodecyl β-D-maltoside and protease inhibitor cocktail).

Immunoblotting

All denaturating Western blotting experiments were performed on 4-12% SDS gels (Invitrogen) with mixture of rabbit polyclonal anti-human KIR4.1 antibodies (Millipore and Alomne lab) using pico or femto ECL detection system (Thermo Scientific). Immunoprecipitated or affinity purified samples were blotted after N-deglycosylation or without deglycosylation. In case of native gel western protein lysate were run on 4-16% bis-tris gels (Invitrogen) in non-denaturating condition according to the manufacturer's protocol.

IgG "Cross-Linking" on Protein-G Beads

Anti-Kir4.1 rat monoclonal antibody targeting the first extracellular domain (mAb Kir4.1-ED), anti-Kir4.1C-terminal mouse monoclonal, control antibodies or purified IgG from KIR4.1 reactive serum were cross-linked on protein G beads as follow. 500 µl protein G beads (GE biosciences) were washed 3 time with PBS. Washed protein G beads were incubated overnight at 4° C. with invert mixing (25-30 rpm) in 15 ml (30 µg/ml) antibody-PBS solution of either of antibodies. IgG bounded protein G beads were washed with PBS 4 time and incubated with 5 ml of 50 mM borate buffer for 2 min and the process was repeated for two times. Further, IgGs bound protein G beads were incubated with cross-linking solution (25 mg DMP in 4.5 ml of 50 mM borate buffer) at 25 degree for 30 minutes. IgG cross-linked protein G beads were washed with 5 ml of ethanolamine and then incubated further with 5 ml of ethanolamine for 1 hour at room temperature. Beads were washed with 5 ml PBS and were stored as 50% slurry. These cross-linked beads were used in 20-30 µl amounts in all immunoprecipitation experiments.

Immunoprecipitation

Protein lysate was pre-cleared with non-IgG bounded protein G beads for non-specific binding. 30 µl antibody "cross linked" protein G beads were incubated with 300 µg of total protein lysate in 300 µl of IP buffer (20 mM tris, 150 mM NaCl, 1 mM EDTA) at 4° C. for 3 hours. Beads were washed with wash buffer (IP buffer supplemented with 0.1% n-Dodecyl β-D-maltoside) two times and further with IP buffer without EDTA two times. Captured protein were eluted two times with 100 µl soft elution buffer (0.2 SDS, 0.1% Tween 20, 50 mM Tris pH 8.0) and further with 100 µl of hard elution buffer (0.2 SDS, 50 mM Tris pH8.0) with an incubation time of 7 minutes each at 25° C. Each eluted fraction was precipitated with the chloroform-methanol method. Precipitated protein were blotted directly or after N-deglycosylation.

N-Deglycosylation

Immunoprecipitated or affinity purified KIR4.1 protein were treated with PNGase (New England Biolab) according manufacturer's instruction. To determine the type of N-linked glycosylation PNGase was used in combination with Endo-H according to manufacturer's instruction.

Immunofluorescence

For immunofluorescence staining either freshly dissected CNS tissue of human origin was snap frozen and embedded in tissue-tek O.C.T (VWR Int., LLC, Radnor, Pa., USA) and Cryo-sectioning was performed at −20° C. to obtain 10 Pm sections or KIR4.1 transfected or wild type HEK293 cells grown in Nunc pre-coated chamber slide were used. After fixation with 100% ice cold methanol for 10 min (in case of tissue) or 4 min (in case of cells), blocking steps were performed with peroxidase, avidin and biotin blocking reagents (Vector Laboratories Inc.) for 15 min each and with 10% goat, mouse or rat serum in PBS-T (0.05% tween-20 in phosphate buffer saline pH 7.0) for 30 min. Sections were then incubated with diluted anti-KIR4.1 rat monoclonal for extracellular loop or rabbit polyclonal for C-terminal (10 ug/ml in PBS-T) overnight at 4° C. After multiple washing steps, sections were incubated with biotin-tagged secondary antibodies for 1 hr at room temperature. Section were further incubated with Avidin-biotin complex (Vector) for 1 hr, with 1 µl of biotinylatedtyramide in PBS with 8.8 mM of $H_2O_2$. All washing steps were performed with PBS-T. Antibody binding was detected with AlexaFluor 488- or AlexaFluor 555-labeled avidin. Nuclear staining was performed using Gold antifade with DAPI (Invitrogen). In case of double staining second primary antibody were used directly without avidin-biotin complex or biotinylated secondary antibodies and probed alexa-488 or 555 labelled anti-goat, anti-rat or anti-rabbit antibodies. Images were taken using a Zeiss Cell Observer microscope with an AxioCamMRm camera (Carl Zeiss MicroImaging, Ltd., Göttingen, Germany).

Cloning, Expression and Purification of KIR4.1

For recombinant KIR4.1 expression in HEK293 or Oli-Neu cells, a full length cDNA encoding human KIR4.1 with C-terminal hexa-histidine tag (his-tag) was synthesized from total human brain mRNA (BD Biosciences, San Jose, Calif.) using 5'-GCG GCC GCA CCA TGA CGT CAG TTG CCA AGG TGT ATT ACA GTC AG-3' (SEQ ID NO: 5) and 5'-CTC GAG TCA GTG GTGGTGGTGGTGGTG GAC ATT GCT GAT GCG CAC-3' (SEQ ID NO: 6) as forward and reverse primers (his-tag encoding sequence is underlined), respectively. Cloning into pcDNA 3.1(+) (Invitrogen) was carried out using NotI and XhoI restriction sites inserted via forward and reverse primers respectively to obtain pcDNA 3.1(+)/KIR4.1 expression construct. HEK 293 cells were transiently transfected (reverse method) with pcDNA 3.1(+)/KIR4.1 using lipofectamine 2000 transfection reagent (Invitrogen) according to the manufacturer's instructions. At 6 hr post-transfection medium was supplemented with 10% FCS and 300 mM barium chloride. At 36 hours post-transfection cells were harvested and washed twice with ice cold PBS. After counting, 2 billion cells were subjected to lysis in 40 ml of 50 mM sodium phosphate buffer pH 7.4 containing 150 mM sodium chloride, 1.0% n-Dodecyl β-D-maltoside, 500 units of Benzonase® nuclease (Sigma) and 1×EDTA free protease inhibitor cocktail (Sigma). Cell lysate was centrifuged at 20,000 rpm, using SS34 rotor on a Sorvall RC6 plus centrifuge for 30 minutes at 4° C. After centrifugation, the supernatant (cleared lysate) was collected and a total of 120-160 mg protein was loaded onto a purification column containing 3 ml of HisPure™ cobalt resin (Pierce) pre-equilibrated with 15 ml of binding buffer (lysis buffer with 0.1% Maltoside). Washing was carried out with 20 ml of washing buffer (lysis buffer with 0.1% Maltoside). Elution of his tagged protein fraction was carried out with 16 ml elution buffer (50 mM sodium phosphate, 150 mM sodium chloride, 150 mM imidazole; pH 6.0). Eluted protein were further fractionated on Hiload 200 pg gel filtration column (GE healthcare) and differentially fractionated KIR4.1 oligomer with low glycosylation were used for ELISA.

KIR4.1 ELISA

KIR4.1 protein is isolated by cobalt bead-based affinity purification (Thermo Scientific, Waltham, Mass.) according to instruction in the method section of cloning, expression and purification of KIR4.1. Affinity purified oligomeric KIR4.1 protein is further fractionated and purified with Hi-load 200 pg gel filtration column (GEBiosciences, Pittsburgh, Pa.). The quality of the oligomeric protein reflects the glycosylation state of KIR4.1 protein expression in white matter (oligodendrocytes) and that may be determined by running protein on 4% to 12% bis-tris gel (Invitrogen, Carlsbad, Calif.) with reducing and nonreducing conditions along with 4% to 16% blue native gel (Invitrogen). Freshly purified protein is preferably used in all assays because KIR4.1 protein is prone to form soluble aggregates at 4° C. or in freezing/thawing cycles. Plate coating is done at 4° C. overnight with 100 µl of 7 µg/ml of non-aggregated oligomeric KIR4.1 in PBS. It is advisable to run titration of protein coating concentration to know exact saturation point by using 20F9 monoclonal antibody (generated against the first extracellular domain of KIR4.1; competing with autoantibodies from the sera of MS patients) as an indicator. Excess protein used above saturation point is prone for aggregation in plate and creates assay variability. After overnight coating plate is washed 3 time with PBST (Phosphate Buffer Saline, 0.5% Tween 20) and blocked with 200 µl of ultra blocking buffer BUF033 (Biorad) for 1 hour at 25° C. Skimmed milk should be avoided as blocker because differences in milk quality might have unpredictable effects on epitope accessibility. After blocking, plates are washed for 3 times with PBST and should be incubated at 25° C. with 100 µl solution of serum or plasma diluted (1:100) in assay diluents buffer BUF037B (Biorad) for 2-3 hour on an orbital shaker (rpm 90). After incubation of sera, plates are washed 5 time with PBST before probing with anti-human IgG secondary antibody (Sigma) diluted (1:10000) in assay diluent buffer BUF037B. Platesare incubated at 25° C. for 1 hour on an orbital shaker (rpm 90). Finally, platesare washed for 5 time with PBST and assay should be develop with 25° C. equilibrated 100 µl TMB solution for 22-25 minutes. Reaction is stopped with 50 µl of 2N $H_2SO_4$. Samples are preferably run in triplicate to determine intra-assay variation. All sera and the sera to determine the cut-off value should be measure in the same assay. None of the samples used in the assays should be ever thawed or refrozen. For best performance average control serum background optical density (OD) should be around 0.5 with maximum limit of 0.8. Maximum inter-assay variation acceptable for the best quality of assay is a CV of less than 8% and intra-assay variation of less than 5%. The cut-off value should be determined for each assay by the OD obtained from the same set of healthy control (HC) donors. The assay is sensitive for serum quality. The average OD as well as the intra and inter assay variation obtained with KIR4.1 antibody negative MS sera should reflect those of sera from patients with other neurological diseases (OND). The assay is preferably with at least 3 different protein preparations to determine inter-assay variability.

EXAMPLE 2

Results

Differential Glycosylation of KIR4.1

Figure 1:
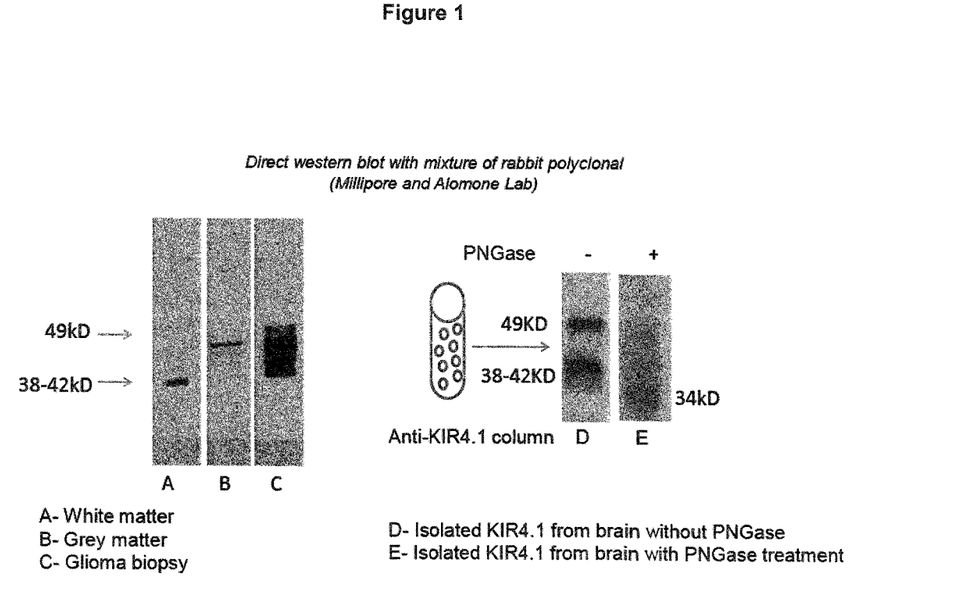
FIG. 1: KIR4.1 differs in white and gray matter by its molecular weight. KIR4.1 was isolated from human brain and treated with PNGase. Note that the differences in KIR4.1 molecular weight arise from glycosylation.

KIR4.1 has an N-glycosylation site, which is located in the larger extracellular domain and can undergo differential glycosylation (see FIG. 1). Analysis of KIR.1 protein from subcortical white and cortical gray matter revealed differences in the molecular weight of the protein. In white matter a 38-42 kD protein, in gray matter a 49-55 kD KIR4.1 protein is dominant. Interestingly, the 49-55 kD KIR4.1 is also dominant in glioma tissue. Deglycosylation with PNGase, which specifically remove N-glycosylation, revealed in both instances a 34 kD protein corresponding to the MW of deglycosylated KIR4.1. This suggests that KIR4.1 is differentially N-glycosylated in the CNS (see FIG. 1).

Antibody competing with the Autoantibody from MS Patients

Figure 2:
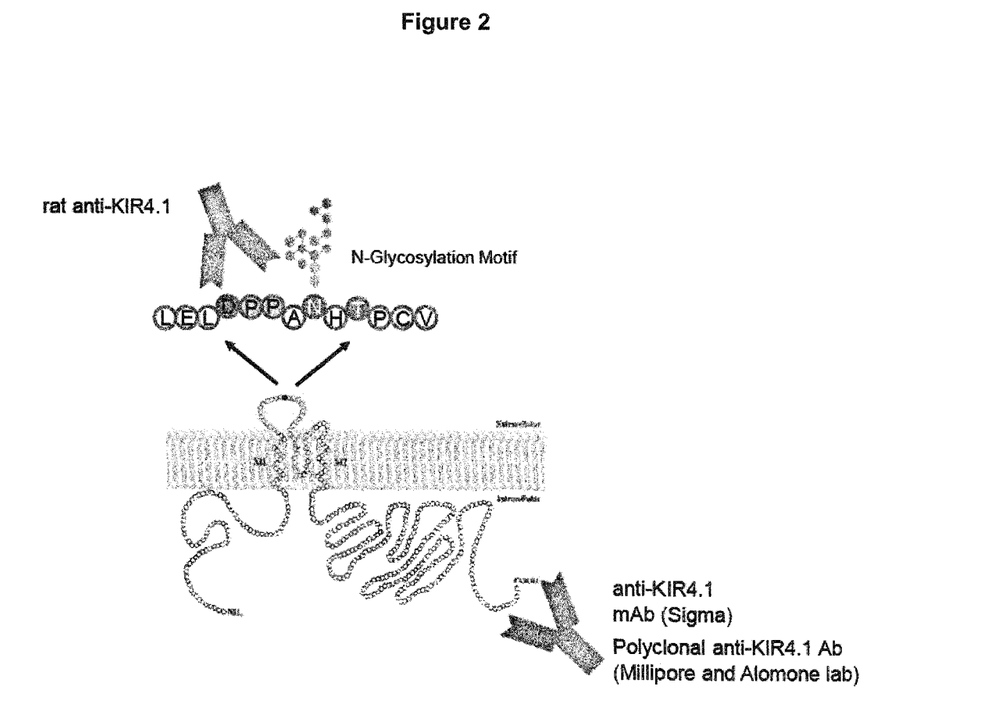
FIG. 2: Binding of KIR4.1 specific antibodies.

To further address this point we generated a rat monoclonal antibody (20F9) against the first extracellular domain of KIR4.1 (FIG. 2). The 20F9 antibody is an example of the antibody in accordance with the fourth aspect of this invention.

The 20F9 antibody precipitates predominantly the lower glycosylated 38-42 kD KIR4.1. In contrast to monoclonal antibodies targeting the C-terminus of KIR4.1, this antibody does not pull the highly glycosylated 49-55 kD KIR4.1 protein. Interestingly, the same binding pattern is observed with KIR4.1 specific antibodies from MS sera (see FIG. 3). These findings suggest that a higher glycosylation of the antigenic epitope might have a steric effect on the antigen-antibody interaction and possibly inhibit antibody binding.

Oligodendrocyte-Specific KIR4.1 Glycosylation

Figure 4:
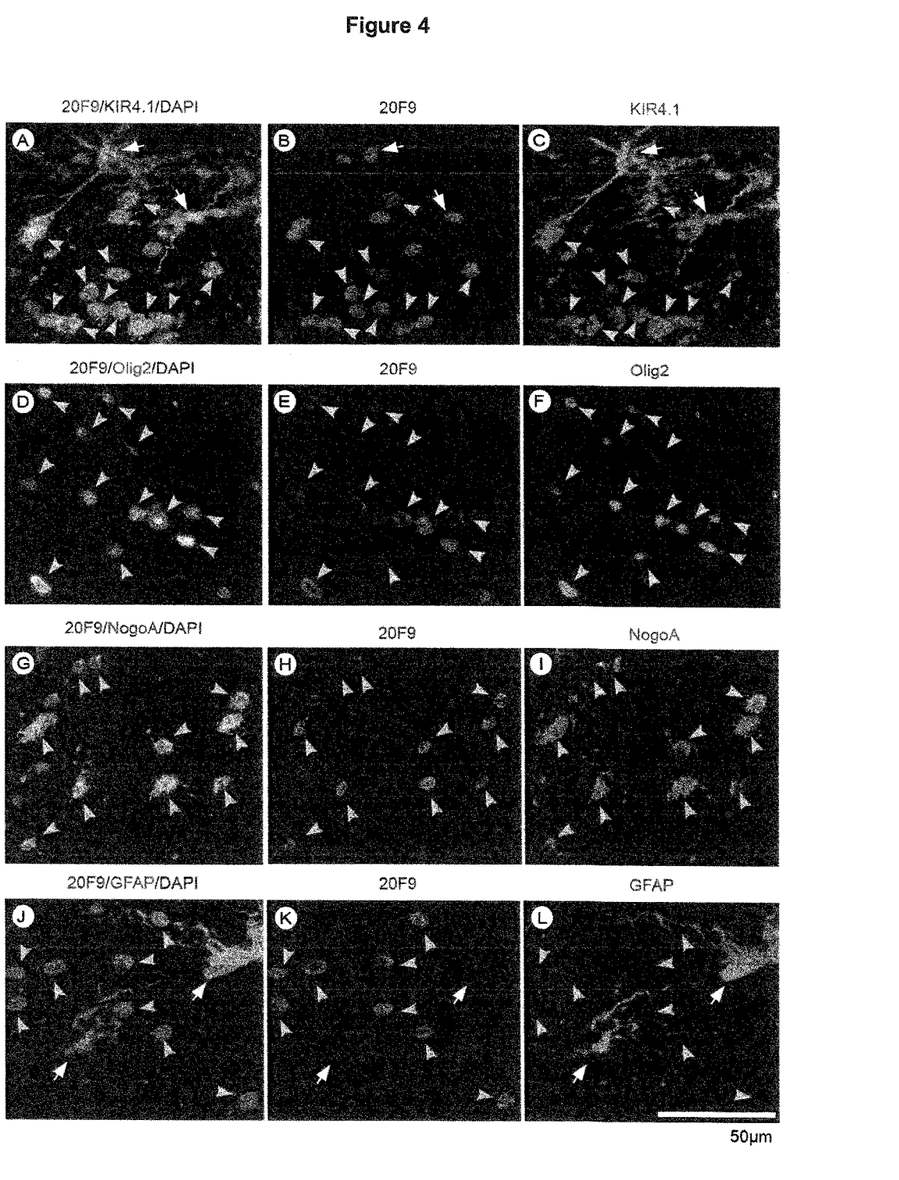

We carried out stainings of human brain tissue with the 20F9 antibody (FIG. 4). This antibody stains predominantly oligodendrocytes and to a lesser extent astrocytes. Interestingly, the staining pattern of this antibody is significantly different from the staining pattern of monoclonal antibodies targeting the C-terminus of KIR4.1. While the latter antibodies stain astrocytes and oligodendrocytes to a similar extent, 20F9 preferentially stains oligodendrocytes and fails to stain astrocytic fibers suggesting that the glycosylation state of KIR4.1 differs between astrocytes and oligodendrocytes.

Figure 5:
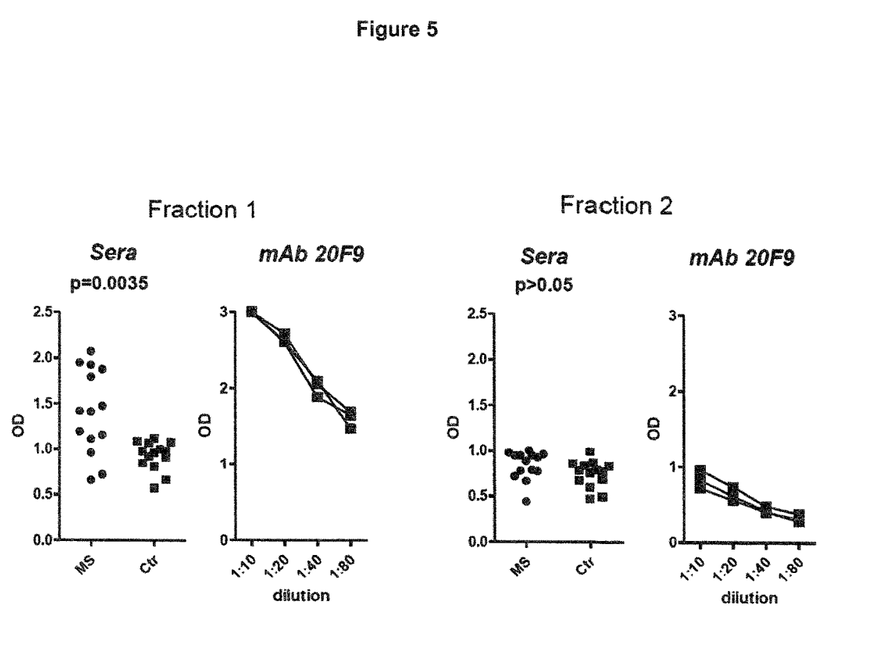
FIG. 5: ELISA with different KIR4.1 fractions isolated from KIR4.1-his tag transfected HEK cells (HEK-KIR4.1-his). Note that significant reactivity was only observed in the eluate, which predominately contained the 38-42 kD variant of KIR4.1. Note that human sera showed a similar reactivity as the rat monoclonal antibody targeting the extracellular domain of KIR4.1. MS, Sera from patients with MS; Ctr, Sera from patients with other neurological diseases. P values are displayed for the comparison between MS and Ctr.

To demonstrate the impact of different glycosylation for antibody binding, we fractionated the recombinant KIR4.1 protein isolated from HEK cells and tested MS sera for reactivity with the different fractions. KIR4.1 antibodies comprised in the serum of MS patients reacted with fraction 1 in which the 38-42 kD protein was enriched but failed to react with fraction 2 that contained predominantly heavily glycosylated KIR4.1 (FIG. 5). Similarly the 20F9 antibody reacted strongly with fraction 1 but much less with fraction 2 although the same protein concentration was used. In line with this finding, MS sera captured 38-42 kD KIR4.1 protein but failed to capture heavily glycosylated KIR4.1 from WT and KIR4.1 transfected HEK cells (FIG. 4).

CONCLUSION

KIR4.1 occurs in several glycosylation states ranging from no glycosylation to heavy glycosylation. Oligodendrocytes express low glycosylated KIR4.1.

The antigenic epitope in the extracellular loop of KIR4.1 contains an N-glycosylation motif, which is prone to complex glycosylation. The extent of glycosylation is depending on cell type and stage.

By generating a monoclonal antibody targeting the same extracellular domain of human KIR4.1 (clone 20F9), which is reactive to human serum IgG, we observed that the level of glycosylation of the extracellular domain has a major impact on antibody binding. 20F9 antibody binds to KIR4.1 only when the protein is weakly or not glycosylated. Heavy glycosylation abrogates binding.

IgG from MS sera behave similar to 20F9 antibody. The antibodies bind to weakly or non-glycosylated KIR4.1 (corresponding to the 38-42 kD variants expressed in oligodendrocytes) but not heavily glycosylated KIR4.1 protein. Assays that do not display the 38-42 KIR4.1 variant may not be able to detect the antibody in MS sera and may therefore provide false negative results.

The invention claimed is:

1. A method for detecting a polypeptide-anti-KIR4.1 complex, the method comprising:
   (a) contacting a sample obtained from a subject with a polypeptide; and
   (b) detecting a polypeptide anti-KIR4.1 antibody complex;
   wherein the polypeptide comprises:
      glycosylated KIR4.1, wherein glycosylation of the large extracellular domain of said KIR4.1 is as in human oligodendrocytes; or
      a subsequence of human KIR4.1 comprising SEQ ID NO: 1 or 2, wherein the N residue of SEQ ID NO: 1 or 2 is glycosylated as the corresponding N residue of the large extracellular domain of KIR4.1 of human oligodendrocytes.

2. The method of claim 1, wherein the polypeptide is a component of an in vitro cell.

3. The method of claim 1, wherein one or more of the following applies:
   (a) KIR4.1 is human KIR4.1;
   (b) said polypeptide is a homotetramer of KIR4.1;
   (c) KIR4.1 consists of the amino acid sequence of SEQ ID NO: 3;
   (d) said extracellular domain consists of the amino acid sequence of SEQ ID NO: 4; and
   (e) glycosylation of the entire protein is as in human oligodendrocytes.

4. The method of claim 1, wherein the polypeptide is obtained from human oligodendrocytes or from a cell line of oligodendrocytic origin.

5. The method of claim 2, wherein the polypeptide is in the cell membrane of the in vitro cell.

* * * * *